United States Patent

Centellas et al.

Patent Number: 5,998,610
Date of Patent: Dec. 7, 1999

[54] SILYLATION PROCESS

[75] Inventors: Victor Centellas; Jose Diago, both of Barcelona, Spain; Johannes Ludescher, Breitenbach, Austria

[73] Assignee: Biochemie Gesellschaft m.b.H., Kundl, Austria

[21] Appl. No.: 08/836,776

[22] PCT Filed: Nov. 2, 1995

[86] PCT No.: PCT/EP95/04562

§ 371 Date: Jul. 25, 1997

§ 102(e) Date: Jul. 25, 1997

[87] PCT Pub. No.: WO96/16067

PCT Pub. Date: May 30, 1996

[30] Foreign Application Priority Data

Nov. 21, 1994 [GB] United Kingdom ............... 9423459

[51] Int. Cl.$^6$ ............... C07D 501/00; C07D 499/48
[52] U.S. Cl. .................................... 540/215; 540/331
[58] Field of Search .................................. 540/215, 331

[56] References Cited

U.S. PATENT DOCUMENTS

| | | |
|---|---|---|
| 4,093,803 | 6/1978 | Cook et al. . |
| 4,138,555 | 2/1979 | Cook et al. . |
| 4,196,205 | 4/1980 | Heymes et al. . |
| 4,224,371 | 9/1980 | Amiard et al. . |
| 4,299,955 | 11/1981 | Falciani et al. . |
| 4,504,657 | 3/1985 | Bouzard et al. . |
| 4,680,390 | 7/1987 | Ochiai et al. . |
| 4,758,556 | 7/1988 | Dürckheimer et al. . |
| 4,973,684 | 11/1990 | Ochia et al. . |
| 5,034,522 | 7/1991 | Schreiber . |
| 5,079,369 | 1/1992 | Takaya et al. . |
| 5,336,776 | 8/1994 | Heymes, et al. . |
| 5,574,154 | 11/1996 | Abu-Nasrieh . |

FOREIGN PATENT DOCUMENTS

| | | |
|---|---|---|
| 0001133 | 8/1978 | European Pat. Off. . |
| 0011513 | 11/1979 | European Pat. Off. . |
| 037380 | 10/1981 | European Pat. Off. . |
| 0169995 | 5/1986 | European Pat. Off. . |
| 0273156 | 7/1988 | European Pat. Off. . |
| 0347777 | 12/1989 | European Pat. Off. . |
| 0439096 | 7/1991 | European Pat. Off. . |
| 439036 | 7/1991 | European Pat. Off. . |
| 2708439 | 7/1978 | Germany . |
| 3539901 | 5/1987 | Germany . |
| 5359689 | 4/1976 | Japan . |
| 5459296 | 10/1977 | Japan . |
| 1073530 | 6/1967 | United Kingdom . |
| 1459807 | 5/1975 | United Kingdom . |
| 2001985 | 8/1978 | United Kingdom . |
| 9117166 | 11/1991 | WIPO . |

OTHER PUBLICATIONS

"Chemical Abstracts", 91, No. 21, p. 175335u, Nov. 19, 1979.
Chem. Abstract, 091, 21 Nov. 19, 1979 Abstract No. 175335, S. Ishiguro, et al.
Chem. Abstract, 091, 25 Dec. 17, 1979 Abstract No. 211349, A. Nakov, et al.
Chem. Abstr. 91:107985 (1979) (on–line accession #1979:507985) of JP54041890.
Chem. Abstr. 119: 180599 (1993) (on–line accession #1993:580599) of PL–154681.
Chem. Abstr. 123:198513 (1995) (on–line accession #1995:789235) of PL–163670.
Chem. Abstr. 123:65823 (1995) (on–line accession #1995:696166) of PL–163938.
Chem. Abs. 110, 237054 1989.
Chem. Abs. 101, 43454 1984.
Chem. Abstr. 89:220887 (1978) (on–line accession #1978:(620887) of DE2708439.
D. J. Korey, et al. J. Parenter, Sci. Technol., 43 (2) 80–3 (1989).
V. Das Gupta, J. Pharm. Sci. 73 (4), 565–7 (1994).
Derwent Abstr. 92–183598/22 of WO 9207840 (Nov. 2, 1990).

*Primary Examiner*—Paul F. Shaver
*Attorney, Agent, or Firm*—Stephen G. Kalinchak; George R. Dohmann

[57] ABSTRACT

A process for the silylation of 6-aminopenicillanic acid or 7-amino-desacetoxy-cephalosporanic acid by silylation in certain carboxylic acid esters and its use in the production of 6-alpha-aminoacyl-penicillins and 7-alpha-aminoacyl-desacetoxy-cephalosporins.

9 Claims, No Drawings

SILYATION PROCESS

This invention relates to a process for the production of silylated 7-amino-desacetoxy-cephalosporanic acid or 6-aminopenicillanic acid by silylation of a 7-amino-desacetoxy-cephalosporanic acid or 6-aminopenicillanic acid and use of the silylated intermediates in the production of a 7-alpha-aminoacyl-desacetoxy-cephalosporin or a 6-alpha-aminoacyl-penicillin.

In EP 439 096 which is incorporated herein by reference, a mixed anhydride process for the production of i.a. ampicillin, amoxicillin, epicillin, cephradine, cephalexin, cefadroxil is described, starting from 6-aminopenicillanic acid (6-APA), or 7-amino-desacetoxy-cephalosporanic acid (7-ADCA).

According to this publication water-immiscible, halogen-free solvents are used in the production of the mixed anhydride resulting in good yields and purities of the products. It is stated that the penicillanic or cephalosporanic acid used as starting material therein may also be silylated, but a process for the silylation of the starting material is not specifically exemplified.

It has now surprisingly been found that silylated starting material used in the process of EP 439 096 for the preparation of products mentioned above results in extremely high yields and purities of the products obtained, if the silylation of the starting material 7-ADCA or 6-APA is carried out in certain carboxylic acid ester solvents.

The invention therefore provides in one aspect a process for the production of a silylated 7-amino-desacetoxy-cephalosporanic acid by silylation of a 7-amino-desacetoxy-cephalosporanic acid in a carboxylic acid ester of formula

wherein independently of each other
X denotes methyl and Y denotes alkyl having at least 3 carbon atoms, or,
X denotes alkyl of at least 2 carbon atoms and Y denotes alkyl.

In another aspect the present invention provides a process for the production of a silylated 6-aminopenicillanic acid by silylation of 6-aminopenicillanic acid in a carboxylic acid ester of formula

wherein independently of each other
X denotes methyl and Y denotes alkyl having at least 3 carbon atoms, or,
X denotes alkyl of at least 2 carbon atoms and Y denotes alkyl, in the presence of a silylation agent other than N,N-bistrimethylsilyl acetamide, N,N'-bistrimethylsilylmalonic acid amide and N,N'-bistrimethylsilyl urea.

Alkyl includes, for example, straight chain or branched $(C_{1-8})$alkyl or $(C_{5-6})$cycloalkyl, in particular straight chain or branched alkyl. Examples include alkyl acetates wherein Y has at least 3 carbon atoms, e.g. 3 to 8 C-atoms and X denotes $C_{1-8}$, preferably $C_{1-6}$, more preferably $C_{1-4}$ alkyl. X may, for example, denote methyl and Y alkyl of at least 3 carbon atoms.

Preferred solvents include propyl acetates or butyl acetates, for example n-butyl acetate or isopropyl acetate.

In a further aspect the present invention provides a process for the production of a silylated 7-amino-desacetoxy-cephalosporanic acid or a silylated 6-aminopenicillanic acid by silylation of 7-amino-desacetoxy-cephalosporanic acid, or 6-aminopenicillanic acid in iso-propylacetate or n-butylacetate.

A compound of formula (I) is used at least as part of the solvent system. The solvent system used may contain more than one compound of formula (I).

The silylation process may be carried out as follows:
The starting material, i.e. 6-APA or 7-ADCA, may be suspended or dissolved in a solvent of formula I as defined above.

If desired a small amount of a co-solvent may be present, for example those known in the art, including organic amides, e.g. formamide or an acetamide, or their N-mono or N,N-dimethyl derivatives, e.g. dimethyl formamide, or N-methylacetamide, N,N-dimethylacetamide, or N-methylpyrrolidine or tetramethylurea. Conveniently the co-solvent comprises about 10 to 50 percent by weight of the solvent system. In particular, however, a co-solvent is not necessarily used.

Silylation agents which are common for the silylation of 7-ADCA or 6-APA may be used; including silanes, such as trichlorosilane or alkylsilanes, such as trialkylmonochlorsilane, e.g. trimethylchlorosilane, dialkyldichlorosilanes; silylated amides, such as bissilylacetamide, e.g. N,O-bis(trimethylsilyl)acetamide, N,N'-bis-trimethylsilylmalonic acid amide, N,N'-bis-trimethylsilylsuccinic acid amide, N-methyl-N-trimethylsilyltrifluoroacatamide; N,N'-bistrimethylsilylmalonic acid diamide, N,N'-bistrimethylsilylsuccinic acid diamide; silylated ureas such as bissilylurea, e.g. N,N-bis(trimethylsilyl)urea, hexamethyl-disilazane. For example, alkylsilanes, hexamethyldisilazane or bissilylacetamides, e.g. alkylsilanes or hexamethyldisilazane, e.g. hexamethyldisilazane are used. The silylation agent may contain one or more silylation agents.

In the case of 6-APA, the process is carried out in one aspect in the presence of a silylation agent other than of N,N-bistrimethylsilyl acetamide, N,N'-bistrimethylsilylmalonic acid amide and N,N'-bistrimethylsilyl urea.

A catalyst common in the field of silylation, such as an amine, in particular a trialkylamine; an amide, for example a cyclic amide, e.g. saccharin; an acidic catalyst, for example an organic acid, e.g. trichloroacetic acid, trifluoroacetic acid, oxalic acid, p-toluenesulphonic acid or an inorganic acid, e.g. hydrochloric acid, sulphuric acid; or a salt, e.g. ammonium sulphate, potassium acetate; may be present in the reaction mixture. It is, however, not necessarily used.

The reaction may be carried out under normal pressure or a vacuum may be applied.

The amount of the silylation agent may depend on whether monosilylated or bissilylated 7-ADCA or 6-APA is desired. In bissilylated 7-ADCA or 6-APA the carboxylic group in position 4 as well as the nitrogen atom in positions 6 or 7, respectively, are silylated. For example an approximately equivalent amount or an excess of the silylating agent may be used, i.e. about 1 to 2 equivalents for each group of the penicillanic acid or of the cephalosporanic acid which is to be silylated. For acylation of the amine group in position 6 or 7, for example monosilylated, or bissilylated, or a mixture of monosilylated and bissilylated 7-ADCA or 6-APA may be used as starting material.

Suitable reaction temperatures include those conventionally used in this field, e.g. from about 0° C. to the refluxing temperature of the solvent used, for example from room temperature to the refluxing temperature. Optionally the starting material may be cooled to lower temperatures when adding the silylation agent, e.g. to −40, −30, −20 or −10° C.

The reaction mixture may be worked up in conventional manner.

The final product may be isolated in conventional manner, e.g. using processes for removing solvents under mild conditions so as not to affect the stability of the silylated 6-aminopenicillanic acid or of the silylated 7-amino-desacetoxy-cephalosporanic acid. Purity may be very high, e.g. above 95 or 98%. The silylated 6-aminopenicillanic acid or the silylated 7-amino-desacetoxy-cephalosporanic acid may be used without working up the reaction mixture and/or without isolation of the silylated product from the reaction mixture, for example in solution, e.g. as starting material in the production of penicillins or desacetoxy-cephalosporins according to the processes of EP 439 096.

The process of the invention as described above is useful in the production of a wide variety of 6-alpha-aminoacyl-penicillins and 7-alpha-aminoacyl-desacetoxy-cephalosporins, such as, for example, ampicillin, amoxicillin, epicillin, cephradine, cephalexin, cefadroxil by N-acylation of silylated 6-APA or 7-ADCA with an acylation agent, including a mixed carboxylic acid anhydride, for example a mixed carboxylic acid anhydride of an alpha-amino acid, which may be a N-substituted vinyl alpha-amino acid, e.g. having the amino group thereof protected as an N-enamine; such as a mixed anhydride of a Dane salt; and deprotecting if appropriate. Included are 6-alpha-aminoacyl-penicillins and 7-alpha-aminoacyl-desacetoxy-cephalosporins in free form or, where such forms exist, in salt and/or solvate form; e.g. substituted 6-acetamido-penicillanic acid derivatives and 7-acetamido-3-desacetoxy-cephem-4-carboxylic acid derivatives and salts and solvates thereof, such as acid addition salts or salts with a base, hydrates or other solvent solvates, e.g. the dimethylformamide solvate. For the purpose of this specification, the term "derivative" denotes, e.g. analogues such as a compound which may bear a substituent at the amino group and/or wherein the carboxylic group is esterified.

In another aspect the invention relates therefore to the use of the process of the invention, i.e. to the use of a process of claim 1 in a process for the production of a 7-alpha-aminoacyl-desacetoxy-cephalosporin and to the use of a process of claim 2 in a process for the production of a 6-alpha-aminoacylpenicillin. The process of claim 1 is, for example useful in the N-acylation of the amine group in position 7 of the silylated 7-ADCA, or in position 6 of the silylated 6-APA, for example in the acylation with a mixed anhydride. In one aspect the product is other than amoxycillin.

In another aspect the present invention provides therefore a process for the production of an 7-aminoacyl-desacetoxy-cephalosporin or an 6-aminacyl-penicillin other than amoxicillin, which comprises (i) producing a silylated 7-amino-desacetoxy-cephalosporanic acid or a silylated 6-aminopenicillanic acid by silylation of a 7-amino-desacetoxy-cephalosporanic acid or a 6-aminopenicillanic acid in a carboxylic acid ester of formula

X—COO—Y (I)

wherein
X denotes methyl and Y denotes alkyl having at least 3 carbon atoms, or,
X denotes alkyl of at least 2 carbon atoms and Y denotes alkyl, and (ii) acylating the silylated 7-amino-desacetoxy-cephalosporanic acid or silylated 6-aminopenicillanic acid with an appropriate acylating agent, for example with a mixed carboxylic acid anhydride, produced by reaction of a salt of an alpha-amino acid, having the amine group thereof protected as an N-enamine with an apropriate acylation agent.

The present invention provides in another aspect a process for the production of amoxicillin which comprises the steps of (i) producing a silylated 7-amino-desacetoxy-cephalosporanic acid or a silylated 6-aminopenicillanic acid by silylation of a 7-amino-desacetoxy-cephalosporanic acid or a 6-aminopenicillanic acid in a carboxylic acid ester of formula

X—COO—Y (I)

wherein
X denotes methyl and Y denotes alkyl having at least 3 carbon atoms, or,
X denotes alkyl of at least 2 carbon atoms and Y denotes alkyl in the presence of a silylation agent other than N,N-bistrimethylsilyl acetamide, N,N'-bistrimethylsilylmalonic acid amide and N,N'-bistrimethylsilyl urea, and (ii) acylating the silylated 7-amino-desacetoxy-cephalosporanic acid or silylated 6-aminopenicillanic acid with an appropriate acylating agent, for example with a mixed carboxylic acid anhydride, produced by reaction of a salt of an alpha-amino acid, having the amine group thereof protected as an N-enamine with an appropriate acylation agent;

and in another aspect, a process for the production of amoxicillin which comprises the steps of (i) producing a silylated 7-amino-desacetoxy-cephalosporanic acid or a silylated 6-aminopenicillanic acid by silylation of a 7-amino-desacetoxy-cephalosporanic acid or a 6-aminopenicillanic acid in a carboxylic acid ester of formula

X—COO—Y (I)

wherein
X denotes methyl and Y denotes alkyl having at least 3 carbon atoms, or,
X denotes alkyl of at least 2 carbon atoms and Y denotes alkyl, and (ii) acylating the silylated 7-amino-desacetoxy-cephalosporanic acid or silylated 6-aminopenicillanic acid with a mixed carboxylic acid anhydride, produced by reaction of a salt of an alpha-amino acid, having the amine group thereof protected as an N-enamine, with an appropriate acylation agent other than a chlorcarbonic acid ester.

A compound of formula I as defined above may be used as solvent also in further steps of the production of a 7-alpha-aminoacyl-cephalosporin or a 6-aminoacylpenicillin, for example in the production of the mixed anhydride, and/or in the acylation of the silylated 6-aminopenicillanic acid or 7-amino-desacetoxy-cephalosporanic acid with the mixed anhydride, and/or in an appropriate deprotection step; for example, the same solvent may be used which is used in step (i).

The product of reaction step (ii) may be, if appropriate, deprotected. If appropriate, a free form of a 6-alpha-aminoacyl-penicillin or a 7-alpha-aminoacyl-desacetoxy-cephalo-sporin obtained may be converted into a salt and/or solvate form or vice versa.

Suitable conditions and reagents in the production of a mixed carboxylic acid anhydride e.g. from a Dane salt, and in the production of 6-alpha-aminoacyl-penicillins and 7-alpha-aminoacyl-desacetoxy-cephalosporins by reaction with 6-APA or 7-ADCA with the mixed anhydride are further disclosed in EP 439 096. For example, a solvent of formula I as defined above is used, e.g. the same, which is used also in the silylation of 6-APA or 7-ADCA, optionally in the presence of a co-solvent as described in EP 439 096. Instead of solubilizing 6-APA or 7-ADCA by salt formation as described in EP 439 096, silylated, preferably bissilylated 6-APA or 7-ADCA is used according to the present invention. Preferred acylation agents in the production of the mixed anhydride include such mentioned in EP 439 096 and further substituted or unsubstituted benzoyl chlorides. Substituted benzoyl chlorides include those having substituents which are inert under the reaction conditions, for example alkyl, preferably $C_{1-4}$, e.g. toluoyl chlorides, for example o-toluoyl chloride. Free hydroxy groups of a Dane salt used may be silylated before the formation of the mixed anhydride and free hydroxy groups of the mixed anhydride may be silylated in the reaction of the mixed anhydride with silylated 6-APA or 7-ADCA as well. Silylation of such hydroxy groups may be effected according to known processes.

The mixed anhydride may be of formula

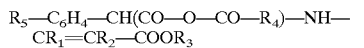

Ia wherein $R_1$ is a $(C_{1-3})$alkyl group, $R_2$ is hydrogen or a $(C_{1-3})$alkyl group, $R_3$ is a $(C_{1-4})$alkyl group, $R_4$ is a $(C_{3-8})$alkyl group or the —CO—$R_4$ group is a benzoyl group, and $R_5$ is hydrogen or an optionally silylated hydroxy group.

The amino group and the carbonyl group attached to the double bond may have the cis configuration.

Usable Dane salts include sodium or potassium D-N-(1-methoxy-carbonylpropen-2-yl)-α-aminophenylacetate, sodium or potassium D-N-(1-ethoxycarbonylpropen-2-yl)-α-aminophenylacetate, sodium or potassium D-N-(1-methoxycarbonylpropen-2-yl)-α-amino-p-hydroxyphenylacetate, or sodium or potassium D-N-(1-ethoxycarbonylpropen-2-yl)-α-amino-p-hydroxyphenylacetate.

Insofar as the production of any starting material used in the process of the invention is not particularly described herein this is known or may be made in analogous manner to known processes.

Deprotection, salt and/or solvate formation may be carried out according to known processes and are not restricted to the processes of EP 439 096.

The use of the silylation process according to the present invention in a process for the production of a 7-aminoacyl-desacetoxy-cephalosporin or for the production of a silylated 6-aminoacylpenicillin has the following advantages:

The starting material is provided in solution in a solvent which, if desired, may be used for all further steps described, for example, in EP 439 096. Throughout the whole process the same solvent may be used, thus avoiding mixtures of solvents which are difficult to separate in a recycling process. The solvent need not be evaporated during the course of the reaction because the final product generally crystallizes and may be filtered off. High yields of, for example at least 88%, for example 90% and high purities, 97% and more, for example 99% and more may be obtained in the production of 6-alpha-aminoacyl-penicillins and 7-alpha-aminoacyl-desacetoxy-cephalosporins.

The following non-limitative examples illustrate the invention. All temperatures are in degrees Centigrade and are uncorrected.

In the examples the following abbreviations are used:

ACI=isopropyl acetate

7-ADCA=7-aminodesacetoxycephalosporanic acid

6-APA=6-aminopenicillanic acid

BSA=N,O-bis(trimethylsilyl)acetamide

Dane salt A=Potassium D-N-(1-ethoxycarbonylpropen-2-yl)-α-aminophenylacetate

Dane salt B=Potassium D-N-(1-methoxycarbonylpropen-2-yl)-α-amino-p-hydroxyphenylacetate DIMAC=N,N-dimethylacetamide DMF=N,N-dimethylformamide HMDS=1,1,1,3,3,3-hexamethyldisilazane IPA=isopropanol NBA=n-butyl acetate The yields are based on 6-APA or 7-ADCA used as starting material, if not otherwise stated. Purity is detected by HPLC on anhydrous basis.

The examples illustrate in step a) silylation of 6-APA or 7-ADCA b) mixed carboxylic acid anhydride formation c) reaction of silylated 6-APA or 7-ADCA of step a) with mixed anhydride of step b) including work up and deprotection to give the product.

EXAMPLE 1

Cephalexin Monohydrate

Step a)

15.0 g of 7-ADCA, 73.5 ml of NBA, 15.39 ml of HMDS and 0.05 g of sacccharin are mixed and the mixture is heated to 70–75°. Vacuum is applied until the mixture starts refluxing. The mixture is kept under reflux at 70–75° for 30 minutes and is cooled to 10–20°. A clear pale brown solution is obtained containing the bissylilated 6-APA. No further starting material is detected.

Step b)

22.55 g of Dane salt A, 75 ml of NBA and 0.012 ml of 4-picoline are mixed and the mixture is cooled to −30°. 8.53 ml of benzoyl chloride are added. The mixture is stirred for 45 minutes at −20/−25° and cooled to −45° to give a mixture containing the mixed carboxylic anhydride.

Step c)

The solution obtained in step a) is added dropwise to the solution obtained in step b) at a temperature of −45 to −30° over 45 minutes and the reaction mixture is stirred for a further 90 minutes at a temperature of −30 to −35°.

The resultant crude mixture containing protected cephalexin is worked up by treatment with a mixture of ice water and concentrated HCl and stirring the reaction mixture for 30 minutes under ice cooling. The aqueous phase is separated off and the organic phase is reextracted with a mixture of concentrated HCl and water. The combined phases are filtered through a filtering aid. The pH value is adjusted to 4.5 to 5.0 by addition of concentrated aqueous ammonia. Crystallized cephalexin monohydrate which is filtrated off, washed with 90% ammonia and dried is obtained. Yield: 89.9%. Purity: 98.2%.

In analogous manner as described in Example 1 but with changes as indicated in the following tables 1 to 3 cephalexin monohydrate is obtained according to Examples 2 to 7:

TABLE 1

Preparation of cephaloxin monohydrate starting from 7-ADCA - Step a) - Production of bissilylated 7-ADCA

|  | Example 2 | Example 3 | Example 4 | Example 5 | Example 6 | Example 7 |
|---|---|---|---|---|---|---|
| ADCA (g) | 5.0 | 15.0 | 5.0 | 15.0 | 15.0 | 15.0 |
| Solvent (ml) | ACI (35.0) | NBA (73.5) | ACI (35.0) | NBA (50.0) | NBA (73.5) | ACI (73.0) |
| Silylation agent | HMDS | HMDS | HMDS | HMDS | HMDS | BSA |
| ml | 5.13 | 15.39 | 5.13 | 15.39 | 15.39 | 19.34 |
| Catalyst (g) | Saccharin (0.01) | Trichloroacetic acid (0.03) | none | Trichloroacetic acid (0.03) | Saccharin (0.01) | none |
| Vaccuum applied | yes | yes | yes | yes | yes | no |
| Temperature | 70–75° | 70–75° | 70–75° | 70–75° | 70–75° | 40° |
| Stirred for (minutes) | 30 | 30 | 30 | 30 | 30 | 150 |
| Bissylilated 7-ADCA obtained in form of | Clear pale yellow solution | Clear pale brown solution | Clear yellow solution | Clear pale brown solution | Clear pale brown solution | Slightly turbide yellow solution |

TABLE 2

Preparation of cephaloxin monohydrate starting from 7-ADCA
Step b) - Production of mixed anhydride; Mixture containing the mixed anhydride obtained

|  | Example 2 | Example 3 | Example 4 | Example 5 | Example 6 | Example 7 |
|---|---|---|---|---|---|---|
| Dane salt A (g) | 7.85 | 22.5 | 7.85 | 22.5 | 22.5 | 22.5 |
| Solvent (ml) | ACI (41.0) | NBA (75.0) | ACI (41.0) | NBA (50.0) | NBA (75.0) | ACI (73.0) |
| Silylation agent | HMDS | HMDS | HMDS | HMDS | HMDS | BSA |
| ml | 5.13 | 15.39 | 5.13 | 15.39 | 15.39 | 19.34 |
| Catalyst (ml) | 4-picoline (0.004) | 4-picoline (0.012) | 4-picoline (0.004) | 4-picoline (0.012) | 4-picoline (0.012) | 4-picoline (0.012) |
| Acylation agent (ml) | benzoyl chloride (2.97) | benzoyl chloride (8.53) | benzoyl chloride (8.53) | o-toluoyl chloride (9.59) | benzoyl chloride (8.53) | benzoyl chloride (8.53) |
| Temperature | –20/–25° | –20/–25° | –30/–35° | –20/–25° | –20/–25° | –20/–25° |
| Stirred for (minutes) | 45 | 45 | 240 | 45 | 45 | 45 |

TABLE 3

Preparation of cephaloxin monohydrate starting from 7-ADCA
Step c) - Production of crystallized cephalexin monohydrate by addition of solution of step a) to solution of step b) and reaction

|  | Example 2 | Example 3 | Example 4 | Example 5 | Example 6 | Example 7 |
|---|---|---|---|---|---|---|
| Addition temperature | –45/–30° | –45/–30° | –45/–30° | –45/–30° | –45/–30° | –45/–30° |
| Addition time (minutes) | 20 | 45 | 20 | 45 | 45 | 45 |
| Stirring temperature | –20/–25° | –30/–35° | –20/–25° | –30/–35° | –30/–35° | –30/–35° |
| Stirring time (minutes) | 240 | 180 | 240 | 180 | 180 | 180 |
| Yield (%) | 87.8 | 90.0 | 87.8 | 90.8 | 89.3 | 87.8 |
| Purity (%) | 98.0 | 98.2 | 98.0 | 97.2 | 98.1 | 98.0 |

EXAMPLE 8

Cefadroxil

Step a) is carried out in analogous manner as described in Example 1 a), but using 50 ml ACI (instead of 73.5 ml NBA) and 0.03 g of trichloroacetic acid (instead of 0.05 g of saccharin). A clear pale brown solution is obtained containing the bissylilated 7-ADCA. No further starting material is detected.

Step b)

25.00 g of Dane salt B, 95 ml of ACI, 95 ml of DMF and 10.28 ml of BSA are mixed and the mixture is stirred vigorously at 25° for 30 minutes. 0.025 ml 4-picoline are added, the mixture is cooled to –50° and 9.50 ml of benzoyl chloride are added. The mixture is stirred for 60 minutes at –45/–50°. A slightly yellow suspension containing the mixed carboxylic acid anhydride is obtained.

Step c)

The solution obtained in step a) is added dropwise to the solution obtained in step b) at a temperature of –45/–35° over 20 minutes and the reaction mixture is stirred for a 3 hours at a temperature of –35/–25°.

The resultant crude mixture containing protected cefadroxil is worked up by treatment with a mixture of ice water and concentrated HCl. The phases are separated and Reextraction with water/HCl is carried out. The combined aqueous phases are treated with additional DMF, the solution is filtered and left overnight in a refrigerator. Crystalline cefadroxil dimethylformamide solvate is obtained, filtered off, washed with acetone and dried. Yield: 83%.

This solvate may be converted into cefadroxil by treatment in aqueous methanol.

EXAMPLE 9

Cefadroxil

Repeating example 8, but with the following step b) instead of step b) of example 8:

25.00 g of Dane salt B, 75 ml of ACI, 8.7 ml of HMDS and 0.015 g of trichloroacetic acid are mixed. The mixture is heated and kept under reflux for 6 hours. A pale yellow suspension is obtained, cooled to room temperature and treated with 75 ml of DMF. After stirring for 15 minutes the mixture is cooled to –50° and 0.025 ml of 4-picoline and 9.50 ml of benzoyl chloride are added. The mixture is stirred for 60 minutes at −45/−50°. A slightly yellow suspension containing the mixed carboxylic acid anhydride is obtained. crystalline cefadroxil dimethylformamide solvate is obtained. Yield: 81%.

EXAMPLE 10

Ampicillin Trihydrate

Step a)

14.0 g of 6-APA, 32 ml of NBA, 13.84 g of BSA and 0.02 g of trichloroacetic acid are mixed and heated to 40°. The mixture is stirred at 40° for 60 minutes and cooled to 25°. A slightly turbid solution containing the bissilylated 6-APA is obtained. No further starting material is detected.

Step b)

0.01 ml of 4picoline are added to a suspension of 21.1 g of Dane salt A and 0.18 g of pivalic acid in 46 ml NBA. The resultant mixture is stirred for 15 minutes at room temperature and cooled to −30°; 8.31 g of pivaloyl chloride are added. The resultant milky suspension is stirred at −15° C. for 60 minutes. 1.8 g of pivalic acid are added and the mixture is cooled to −45°. A mixture containing the mixed carboxylic acid anhydride is obtained.

Step c)

The mixture obtained in step a) is added dropwise to the mixture obtained in step b) at a temperature of −45/−35°. The resultant mixture is stirred for 2 hours at a temperature of −15/−35°. The resultant crude protected ampicillin mixture is worked up by treating with a mixture of ice-water and concentrated hydrochloric acid and stirred for 20 minutes while cooling with ice. The aqueous phase is separated off and the organic phase is reextracted with a mixture of water and concentrated hydrochloric acid. The combined aqueous phases are treated with concentrated aqueous sodium hydroxide to a pH of 4.5/5.5. Ampicillin trihydrate crystallizes out of the reaction mixture overnight in a refrigerator, the crystals are isolated, washed with IPA 88% and dried. Yield 89.0%, Purity 98.4%.

EXAMPLE 11

Ampicillin Trihydrate

Step a) 14.0 g of 6-APA, 32 ml of NBA, 14.2 ml of HMDS and 0.03 g of trichloroacetic acid are mixed and heated to 70–80°. Vacuum is applied until the mixture starts refluxing. The mixture is kept under reflux at 70–80° for 60 minutes and then cooled to 10°. A clear yellow solution containing bissylilated 6-APA is obtained.

Step b)

0.01 ml of 4-picoline are added to a suspension of 21.1 g of Dane salt A in 51 ml of NBA. The resultant mixture is stirred for 15 minutes at room temperature and cooled to −30°; 10.65 g of o-toluoyl chloride are added. The resultant suspension is stirred at a temperature of −20 to −25° for 60 minutes and cooled to 45°. A mixture containing the mixed carboxylic acid anhydride is obtained.

Step c)

The mixture obtained in step a) is added dropwise to the mixture obtained in step b) at a temperature of −45/−30°. The resultant mixture is stirred for 90 minutes at a temperature of −35/−20°. The resultant crude protected ampicillin mixture is worked up analogous as described in Example 10 c). Crystalline ampicillin trihydrate is obtained. Yield 88.5%. Purity 98.0%.

EXAMPLE 12

Ampicillin Trihydrate

Repeating Example 10, but using in step b) 0.01 ml of 3,5-lutidine instead of 0.01 ml of 4-picoline and carrying out step c in analogous manner as described in Example 11 c), but stirring the mixture for 150 minutes (instead for 90 minutes), crystalline ampicillin trihydrate is obtained. Yield 89%, Purity 98.1%.

EXAMPLE 13

Amoxicillin Trihydrate

Step a) is carried out in analogous manner as described in Example 11 a), but heating to 80 to 90° (instead of 70 to 80°). A clear yellow solution containing bissilylated 6-APA is obtained. No further starting material is detected.

Step b)

0.03 ml of 4picoline are added to a suspension of 21.8 g of Dane salt B in 64 ml of NBA and 5 ml of DIMAC. The resultant mixture is stirred for 15 minutes at room temperature, cooled to −25° and 8.62 g of pivaloyl chloride are added. The resultant suspension is stirred at a temperature of −20° for 45 minutes. 3 g pivalic acid are added and the mixture is cooled to −40°. A mixture containing the mixed carboxylic acid anhydride is obtained.

Step c)

The solution obtained in step a) is added dropwise to the mixture obtained in step b) at a temperature of −45/−30°. The mixture is stirred for 90 minutes at a temperature of −30/−15°. The resultant crude protected amoxicillin mixture is worked up by treatment with a mixture of ice-water and concentrated hydrochloric acid and stirring for 30 minutes while cooling with ice. The aqueous phase is separated off and the organic phase reextracted with water. The combined aqueous phases are treated with concentrated aqueous sodium hydroxide to a pH of 4.5/5.5. Crystalline amoxicillin trihydrate is isolated as described in Example 10 c). Yield 88.4%. Purity 99.3%.

EXAMPLE 14

Amoxicillin Trihydrate

Carrying out step a) in analogous manner as described in Example 10 a), but using 32 ml ACI instead of 32 ml NBA, step b) in analogous manner as described in Example 13 b), but using 64 ml of ACI instead of NBA and step c) in analogous manner as described in Example 10 c), crystalline amoxicillin trihydrate is obtained. Yield 87.8%, Purity 99.1%.

We claim:

1. A process for the production of a silylated 7-amnino-desacetoxy-cephalosporanic acid which comprises silylation of a 7-amino-desacetoxy-cephalosporanic acid in a carboxylic acid ester of formula $$X\text{—}COO\text{—}Y \qquad (I)$$

wherein

X denotes methyl and Y denotes $C_3$–$C_8$ alkyl.

2. A process for the production of a silylated 6-aminopenicillanic acid which comprises silylation of 6-amninopenicillanic acid in a carboxylic acid ester of formula $$X\text{—}COO\text{—}Y \qquad (I)$$

wherein

X denotes methyl and Y denotes $C_3$–$C_8$ alkyl, in the presence of a silylation agent other than N,N-bistrimethylsilyl acetamide, N,N'-bistrimethylsilylmalonic acid amide and N,N'-bistrimethylsilyl urea.

3. A process of claim 1 wherein the carboxylic acid ester is a propyl acetate or a butylacetate.

4. A process for the production of a silylated 7-amino-desacetoxy-cephalosporanic acid or a silylated 6-aminopenicillanic acid by silylation of 7-amino-desacetoxy-cephalosporanic acid, or 6-aminopenicillanic acid in iso-propylacetate or n-butylacetate.

5. A process for the production of an 7-aminoacyl-desacetoxy-cephalosporin or an 6-aminoacyl-penicillin other than amoxicillin, which comprises
   (i) producing a silylated 7-amino-desacetoxy-cephalosporanic acid or a silylated 6-amino-penicillanic acid by silylation of a 7-amino-desacetoxy-cephalosporanic acid or a 6-aminopenicillanic acid in a carboxylic acid ester of formula $$X\text{—}COO\text{—}Y \qquad (I)$$

wherein
   X denotes methyl and Y denotes $C_3$–$C_8$ alkyl, and
   (ii) acylating the silylated 7-amino-desacetoxy-cephalosporanic acid or silylated 6-amino-penicillanic acid with an appropriate acylating agent.

6. A process for the production of amoxicillin which comprises the steps of
   (i) producing a silylated 6-amino-penicillanic acid by silylation of a 7-amino-desacetoxy-cephalosporanic acid or a 6-aminopenicillanic acid in a carboxylic acid ester of formula $$X\text{—}COO\text{—}Y \qquad (I)$$

wherein
   X denotes methyl and Y denotes $C_3$–$C_8$ alkyl in the presence of a silylation agent other than N,N-bistrimethylsilyl acetamide, N,N'-bistrimethylsilylmalonic acid amide and N,N'-bistrimethylsilyl urea, and (ii) acylating the silylated 7-amino-desacetoxy-cephalosporanic acid or silylated 6-amino-penicillanic acid with a mixed carboxylic acid anhydride with an appropriate acylating agent.

7. A process for the production of amoxicillin which comprises the steps of
   (i) producing a silylated 6-amino-penicillanic acid by silylation of a 7-amino-desacetoxy-cephalosporanic acid or a 6-aminopenicillanic acid in a carboxylic acid ester of formula $$X\text{—}COO\text{—}Y \qquad (I)$$

wherein
   X denotes methyl and Y denotes $C_3$–$C_8$ alkyl, and
   (ii) acylating the silylated 7-amino-desacetoxy-cephalosporanic acid or silylated 6-amino-penicillanic acid with a mixed carboxylic acid anhydride, produced by reaction of a salt of an alpha-amino acid, having the amine group thereof protected as an N-enamine, with an appropriate acylation agent other than a chlorcarbonic acid ester.

8. A process for the production of a 7-aminoacyl-desacetoxy-cephalosporin or a 6-aminoacyl-penicillin, which comprises
   (i) silylating a 7-aminoacyl-desacetoxy-cephalosporanic acid or a 6-aminoacyl-penicillanic acid in isopropylacetate or n-butylacetate to produce a silylated 7-aminoacyl-desacetoxy-cephalosporanic acid or a silylated 6-aminoacyl-penicillanic acid, and
   (ii) acylating the silylated 7-aminoacyl-desacetoxy-cephalosporanic acid or the silylated 6-aminoacyl-penicillanic acid.

9. A process of claim 2 wherein the carboxylic acid ester is a propyl acetate or a butyl acetate.

* * * * *

UNITED STATES PATENT AND TRADEMARK OFFICE
CERTIFICATE OF CORRECTION

PATENT NO. : 5,998,610 Page 1 of 1
APPLICATION NO. : 08/836776
DATED : December 7, 1999
INVENTOR(S) : Centellas et al.

It is certified that error appears in the above-identified patent and that said Letters Patent is hereby corrected as shown below:

Title page, item [22], "PCT Filed: Nov. 2, 1995" should read -- PCT Filed: Nov. 20, 1995 --.

COLUMN 10
    Line 47, claim 1, "7-amnino desacetoxy-cephalosporanic" should read -- 7-amino-desacetoxy-cephalosporanic --.
    Line 58, claim 2, "6-amninopenicillanic" should read -- 6-aminopenicillanic --.

COLUMN 12
    Lines 8-9, claim 7, "7-amino-desacetoxy-cephalosporanic acid or a" should be deleted.

Signed and Sealed this

Sixth Day of November, 2007

JON W. DUDAS
*Director of the United States Patent and Trademark Office*